United States Patent

Bathe et al.

Patent Number: 6,164,276
Date of Patent: Dec. 26, 2000

[54] ACCURATE DOSE NITRIC OXIDE PULSE DELIVERY DEVICE WITH MONITORING AND ALARMS

[75] Inventors: Duncan P. L. Bathe, Madison; Frederick J. Montgomery, Sun Prairie, both of Wis.

[73] Assignee: Datex-Ohmeda, Inc., Liberty Corner, N.J.

[21] Appl. No.: 09/084,710

[22] Filed: May 26, 1998

Related U.S. Application Data

[63] Continuation-in-part of application No. 08/857,924, May 16, 1997, abandoned.

[51] Int. Cl.$^7$ .......................... A61M 16/00; A62B 27/00; A62B 9/00; G08B 3/00
[52] U.S. Cl. ................................ 128/202.22; 128/203.12; 128/203.14; 128/204.21; 128/204.23; 128/205.23
[58] Field of Search .......................... 128/202.22, 203.12, 128/203.14, 204.18, 204.23, 205.23, 205.24, 205.25, 204.21

[56] References Cited

U.S. PATENT DOCUMENTS

| | | | |
|---|---|---|---|
| 4,462,398 | 7/1984 | Durkan et al. . | |
| 4,665,911 | 5/1987 | Williams et al. | 128/204.21 |
| 4,823,788 | 4/1989 | Smith et al. . | |
| 4,932,402 | 6/1990 | Snook et al. | 128/204.23 |
| 5,005,570 | 4/1991 | Perkins . | |
| 5,038,771 | 8/1991 | Dietz . | |
| 5,531,218 | 7/1996 | Krebs | 128/203.12 |
| 5,558,083 | 9/1996 | Bathe et al. . | |
| 5,558,086 | 9/1996 | Smith et al. | 128/204.26 |
| 5,603,315 | 2/1997 | Sasso, Jr. . | |
| 5,732,693 | 3/1998 | Bathe et al. | 128/203.12 |
| 5,752,504 | 5/1998 | Bathe | 128/203.12 |
| 5,794,615 | 8/1998 | Estes | 128/204.23 |
| 5,839,433 | 11/1998 | Higenbottam | 128/204.21 |
| 5,839,434 | 11/1998 | Enterline | 128/204.23 |
| 5,845,633 | 12/1998 | Psaros | 128/200.24 |
| 5,865,174 | 2/1999 | Kloeppel | 128/204.23 |
| 6,089,229 | 7/2000 | Bathe et al. | 128/204.21 |

FOREIGN PATENT DOCUMENTS

| | | |
|---|---|---|
| 602734 | 6/1994 | European Pat. Off. . |
| 2240849 | 8/1991 | United Kingdom . |
| 95/10315 | 4/1995 | WIPO . |
| 95/28193 | 10/1995 | WIPO . |

OTHER PUBLICATIONS

"Inhaled Nitric Oxide in Persistent Pulmonary Hypertension of the Newborn" and "Low–dose Inhalational Nitric Oxide in Persistent Pulmonary Hypertension of the Newborn"—The Lancet, vol. 340, Oct. 1992, pp. 818–820.

"Inhaled NO–the past, the present and the future"—Anesthesiology, vol. 78 (1993), pp. 413–416.

"Pulsed delivery of inhaled nitric oxide to patients with primary pulmonary hypertension"—Channick et al.—Chest/109 Jun. 1996, pp. 1545–1549.

*Primary Examiner*—John G. Weiss
*Assistant Examiner*—Joseph F. Weiss
*Attorney, Agent, or Firm*—Andrus, Sceales, Starke & Sawall, LLP

[57] ABSTRACT

A respiratory therapy apparatus that delivers a predetermined precise volume of a therapeutic gas to a patient upon each inhalation of the patient. The apparatus has a flow sensing device and a valve that opens and closes to deliver the pulse to the patient. A CPU controls the open time of the valve and also uses the flow to the patient determined by the flow sensing device and the time the valve is in the open position to determine the volume of therapeutic gas to the patient. A user input device communicates a user desired volume to be delivered to the patient and the CPU compares the user input desired volume with the calculated volume and adjusts the time the valve is in the open position to cause the apparatus to deliver to the patient the precise desired volume inputted by the user. In one embodiment the system senses and used the ambient temperature and ambient pressure to determine the correct volume of gas delivered to the patient. The apparatus thus provides a precise volume of therapeutic gas to the patient during each inhalation independent of supply pressure of the therapeutic gas, the ambient pressure, ambient temperature or the size of the inhalation.

11 Claims, 2 Drawing Sheets

6,164,276

ACCURATE DOSE NITRIC OXIDE PULSE DELIVERY DEVICE WITH MONITORING AND ALARMS

RELATED APPLICATIONS

The present application is a continuation-in-part of U.S. patent application Ser. No. 08/857,924, filed May 16, 1997 now ABN.

BACKGROUND

This invention relates to the administration of a therapeutic gas such as nitric oxide (NO) to patients for therapeutic effect. In particular, it relates to a system wherein a controlled, predetermined dose of NO is provided to the patient with each inhalation by the patient.

The function of the administration of NO has been fairly widely published and typical articles appeared in The Lancet, Vol. 340, October 1992 at pages 818–820 entitled "Inhaled Nitric Oxide in Persistent Pulmonary Hypertension of the Newborn" and "Low-dose Inhalation Nitric Oxide in Persistent Pulmonary Hypertension of the Newborn" and in Anesthesiology, Vol. 78, pgs. 413–416 (1993), entitled "Inhaled NO-the past, the present and the future".

The actual administration of NO is generally carried out by its introduction into the patient as a gas and commercially available supplies are provided in cylinders under pressure and may be at pressures of about 2000 psi and consist of a predetermined mixture of NO in a carrier gas such as nitrogen. A pressure regulator is therefore used to reduce the pressure of the supply cylinder to working levels for introduction to a patient.

The concentration administered to a patient will vary according to the patient and the need for the therapy but will generally include concentrations at or lower than 100 ppm. There is, of course, a need for that concentration to be precisely metered to the patient since an excess of NO can be harmful to the patient.

One current known method and apparatus for the administration of NO to patients is described in U.S. Pat. No. 5,558,083 where a system is provided that can be added to any ventilator and which will meter in the desired concentration of NO into the gas supplied from that ventilator.

Various other delivery devices have also been used that respond to the patient attempting to inhale to deliver a pulsed dose of NO to the patient and such pulsing devices have also been shown to have therapeutic effect on the patient, for example, as described in Higenbottam PCT patent application WO 95/10315 and the publication of Channick et al "Pulsed delivery of inhaled nitric oxide to patients with primary pulmonary hypertension", Chest/109/June 1996. In such pulsatile dosing devices, a pulse of NO is administered to the patient as the patient inhales spontaneously.

The inhalation pulsing type devices are typically shown and described in Durkan, U.S. Pat. No. 4,462,398, however the Durkan device has certain limitations and was designed for the administration of oxygen and not NO. Again, further devices are known, based somewhat on the Durkan device, such as described in Perkins U.S. Pat. No. 5,005,570 and Dietz U.S. Pat. No. 5,038,771. Again, however, the devices were principally designed for use in the administration of oxygen. One of the properties of NO is that it has a toxic effect at high concentrations while having its beneficial therapeutic effect at low concentrations. Additional hazards also exist from hypoxia with over delivery of NO as the balance gas for NO is nitrogen, high pulmonary arterial pressures which result in low $PaO_2$ from under delivery of NO, and the conversion of NO in the presence of oxygen to nitrogen dioxide, $NO_2$, which is a more toxic compound. Nitric oxide systems, therefore, require additional safeguards and control than with devices designed for the delivery of oxygen.

Basically, of the types known, the Durkan and Perkins approach to administration is based on the time that a flow control valve is open and thus the time that the gas is administered to the patient. With such a system, however, the device does not provide a fixed volume of gas to the patient under all conditions as a variation in input pressure, ambient temperature or altitude will result in a higher or lower flow of gas through the valve. Accordingly, with a fixed time interval, the differing flow will result in differing volumes being delivered per breath to the patient.

As an example, with a timed interval device the cylinder of gas will generally be reduced in pressure as the administration of the gas is carried out. The regulator that reduces the cylinder pressure to a working pressure, generally puts out a decreased pressure as the cylinder pressure is lowered, that is, as a direct function. Since that pressure downstream of the regulator varies, so does the flow to the patient and the actual volume dose of NO to the patient is, therefore, not constant with a constant timed dosage, but varies as the cylinder pressure varies.

The Dietz patent takes a differing approach, and which varies the time the valve is opened based on the size of the previous breath of the patient. Again, the volume delivered per breath is variable due to the input pressure and the altitude and is further dependent on the size of the breath itself, i.e. the larger the breath, the higher the dose provided to the patient. Such may not be required for NO therapy to the patient.

One further problem with the typical prior art devices is that there is no safety system to indicate when the timing valve has failed and thus, the patient may not be receiving the needed therapy from the device or may be receiving an excess of therapy.

As a further shortcoming of current known systems, the ambient temperature and pressure also have an effect on the dose of gas delivered during any timed pulse and thus can thereby affect the treatment of the individual that is receiving the NO therapy. The current devices do not take the ambient temperature or pressure into account in providing the pulse to the patient and therefore such devices can introduce inaccuracies in the particular dosage. With the use of NO, however, such inaccuracies can create a harmful situation to the patient.

Accordingly, with the use of such current devices for administering NO, the actual dose of the NO to the patient may vary and the exact dose is basically unknown, thus the control of the therapy is somewhat difficult and a need exists for more precise control of the dose of NO administered per breath and better alarms are required to indicate if there is unsafe over or under delivery of the NO therapy.

SUMMARY OF THE INVENTION

In accordance with the present invention, there is provided a nitric oxide delivery system where a constant dose of NO is administered to the patient regardless of changes in the cylinder pressure, ambient temperature or other factors affecting the delivery. The NO can be delivered in a cylinder mixed with a carrier gas such a nitrogen without affecting the constant dose administered.

In carrying out the present invention, a sensing device detects the start of a patient's spontaneous breathing and the system injects a predetermined desired dose of NO to the patient at the start of that breath by the opening of a control valve. The source of the NO containing gas may be a cylinder containing a predetermined concentration of NO in a balance gas such as nitrogen. That predetermined desired dose may be selected by the user with some input device or may be factory set by the manufacturer of the equipment. In the preferred embodiment, the sensing device may be mounted within the delivery system downstream of the control valve and upstream of the outlet to the patient. The patient is connected to the outlet of the delivery system by a single connection such as a nasal cannula or similar device for actual administration of the therapeutic gas to the patient.

A central processing unit (CPU) provides the control of a control valve upon the sensing device indicating the start of an inhalation. The CPU energizes the control valve from the normally closed position, where no therapeutic gas is being delivered to the patient, to the energized, open position, where gas is supplied to the patient for a calculated period of time and at the end of that time period, the CPU switches the control valve from the energized, open position, back to the de-energized, closed position. The flow of NO containing gas flows through a fixed restrictor that is located between the control valve and the patient.

In a first embodiment, the amount of the time during which the control valve is open is calculated by the CPU based on the pressure delivered from the regulator, the ambient pressure, the characteristics of the restrictor and the predetermined desired volume of NO. In this embodiment, an absolute pressure transducer is used to determine and monitor the pressure upstream of the fixed restrictor. Such transducers operate off a base of 0 psia and therefore take into account the ambient pressure in the area. Since the flow through a fixed restrictor is directly proportional to the absolute pressure upstream of the restrictor, the measurement of that absolute pressure is used by the CPU to precisely measure the flow of NO containing gas to the patient.

The flow through the fixed restrictor is therefore a known value based on the absolute pressure upstream of the restrictor and the known characteristics of the particular restrictor available from the supplier of that restrictor. Accordingly, the measurement of the pressure, along with the known pressure flow characteristics of the restrictor will accurately give the flow of NO containing therapeutic gas delivered to the patient during the time period the control valve is in the open position. That determination of flow can then be integrated with respect to the time the control valve is open by the CPU to calculate the actual dose of NO and carrier gas delivered to the patient.

As can then be seen, given the dose so calculated, that dose can be compared to the predetermined desired dose set by the user or established in the delivery system and the control valve open time varied by the CPU to correct for any differences. Thus, the precise dose of NO delivered to the patent can be controlled with respect to each breath of the patient.

At start up, the system CPU may start with the pressure of the previous use of the device or, alternatively, can arbitrarily pick out an absolute pressure that is known to be around the value that is inputted to the fixed restrictor, i.e. around 50 psia. After start-up, the unit will cycle for a few times so that it can calculate the actual values of the volume of gas to the patient and compare that value with the value set by the user and eventually modify the time the control valve is open during each inhalation to have the system provide the exact predetermined desired volume to the patient and alarm conditions can be given if the dose is outside the predetermined safe limits.

In the preferred embodiment, the system determines the amount of time that the control valve is opened by a correction based upon the ambient temperature and ambient pressure at the location of the patient. Accordingly, in this embodiment, the system is calibrated during manufacture and a calibration curve is determined at the factory under known ambient pressure and temperature conditions and the volume of gas $V_{CAL}$ is determined based on those conditions for the opening times of the control valve. That calibration curve is incorporated into the device such that, at the end use of the pulse device, the ambient temperature and ambient pressures are sensed and the volume of the gas delivered corrected in accordance with those ambient conditions.

In such embodiment, therefore, the dose is thus corrected for ambient temperature and pressure so that the dose actually set by the user will be delivered to the patient.

As in the prior embodiment, after the initial determination of the time the control valve is opened, the system monitors to see if the dose of gas actually administered to the patient is correct. In this embodiment, the flow through the control valve is accurately determined by an equation that utilizes the absolute pressure upstream of an orifice along with the temperature of the gas passing through the orifice and the known pressure flow characteristics of the orifice itself. Thus, by using those values, the precise flow through the orifice can be determined and thus integrated with respect to the time the control valve is open to determine the exact volume of gas delivered to the patient. Again, that actual dose delivered is then compared against the dose set by the user and a further adjustment made to the time the control valve is in its open position delivering NO containing therapeutic gas to the patient.

Since the pulse delivery device has both a calibrating curve set dose and an independent dose measuring means, various controls and failure alarms can be built into the system. For example, it is possible to detect the failure of the control valve based on data from the control pressure and the timing sequence. If there is no rise in the value of the control pressure by a known amount, based on the minimum supply pressure and the valve has been given a signal to open, then the system can detect a failure to deliver therapy. Conversely, if the control pressure does not reduce by a known amount, again based on the minimum supply pressure, and the valve has been given a signal to close, then the system can detect an over delivery failure. Also, the system can detect when a patient trigger has not occurred after a predetermined time or a user set time from either start up or the last breath and which can, by the CPU, trigger an alarm.

DETAILED DESCRIPTION OF THE INVENTION

Figure 1:
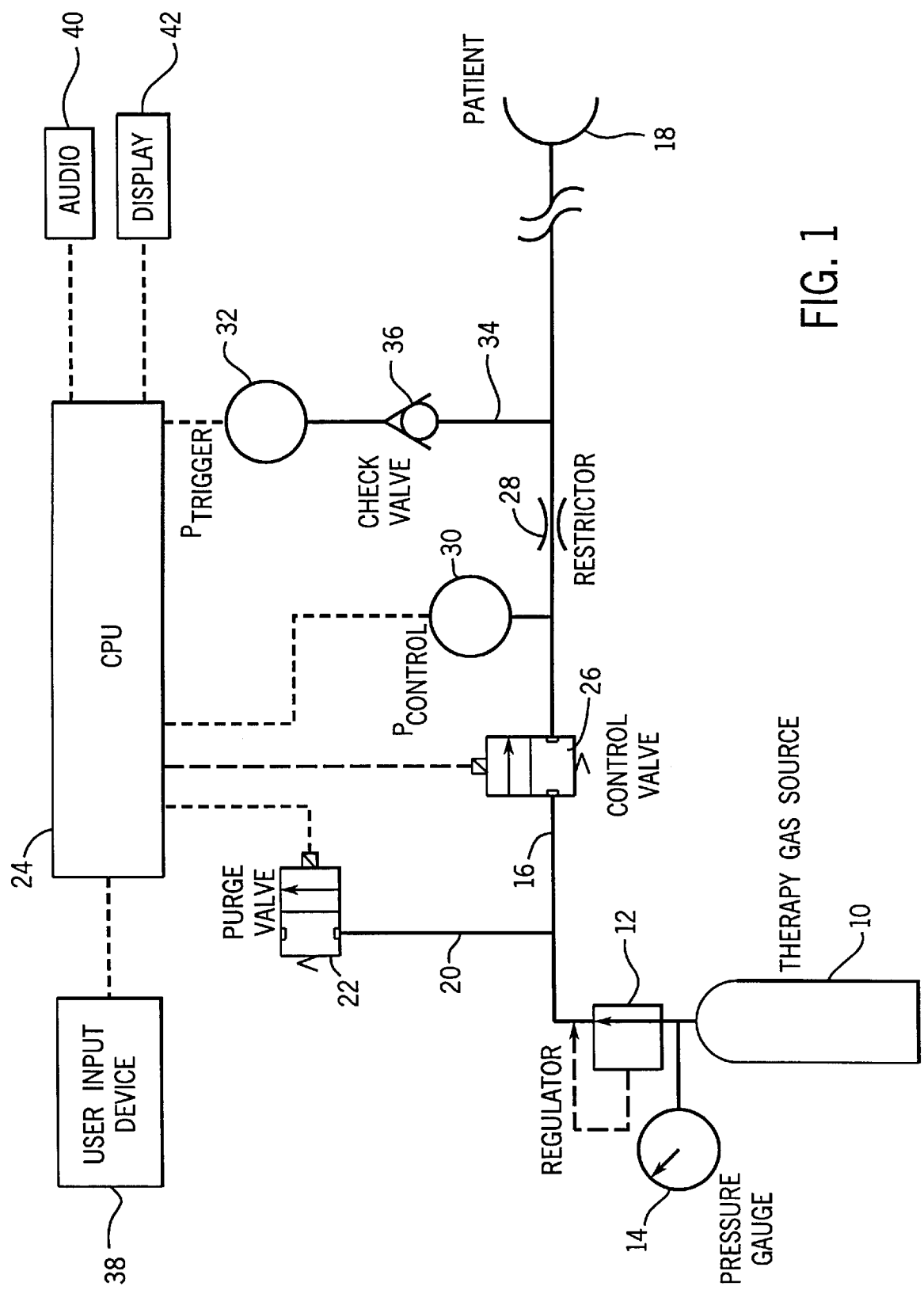
FIG. 1 is a schematic view of a NO delivery system constructed in accordance with the present invention.

Turning now to FIG. 1, there is shown a schematic view of a pulsed dosing NO delivery apparatus constructed in accordance with one embodiment of the present invention.

A gas cylinder 10 is provided containing the therapeutic amount of nitric oxide. Preferably the NO gas is mixed with a balance or carrier gas such as nitrogen and the concentration may be in the order of 100 ppm. The NO in nitrogen gas is available commercially in cylinders at pressures of approximately 2000 psig.

A pressure regulator 12 reduces the cylinder pressure down to a working pressure for use with the present system and that pressure may be in the order of about 50 psig. A pressure gauge 14 is generally provided on the pressure regulator 12 in order to keep track of the pressure within the gas cylinder 10.

A conduit 16 carries the NO containing therapy gas from the pressure regulator 12 through to a patient 18 where the NO containing therapy gas is administered to the patient 18 by means such as a nasal cannula (not shown). Teed off from the conduit 16 is a purge line 20 and a purge valve 22. As can be seen, the purge valve 22 is normally in the non-energized position blocking the flow of gas therethrough and is activated by a central processing unit (CPU) 24 to open the purge valve 22 to clear certain portions of the conduit 16 as well as pressure regulator 12 of gas. Thus, when the gas cylinder 10 is opened, on initial use of the equipment, the NO containing therapy gas flows through the pressure regulator 12, a portion of the conduit 16 and, the purge line 20 and is exhausted out the purge valve 22 to rid those passages of air and thus to make sure that the oxygen present in air cannot act on the NO to create $NO_2$, a toxic substance.

Operation of the purge valve 22 may be immediate by the CPU 24 upon start up of the apparatus or may be accomplished manually with a prompt from a display operated by the CPU 24.

A control valve 26 controls the flow of NO containing therapy gas from the gas cylinder 10 to the patient 18 and is a solenoid controlled valve operated by signal from the CPU 24. Again, for safety, the control valve 26 is normally closed and is moved to its open position when a signal energizes the valve by CPU 24. As will be explained, the time during which the control valve is in the open position controls the volume of NO containing therapy gas delivered to the patient 18.

A fixed restrictor 28 is also provided in the conduit 16 and may be a commercially available restrictor and which is provided with the pressure to flow characteristics by the supplier. Just upstream of the fixed restrictor 28 is an absolute pressure transducer 30 which senses the absolute pressure in the conduit 16 as $P_{control}$. That pressure is also communicated to the CPU 24 as will be later explained. The absolute pressure transducer 30 is of the type that operates off a base of zero psi and therefore it reads the absolute pressure within the conduit 16 at the point just upstream of the fixed restrictor 28. By the absolute pressure, the reading takes into account the ambient pressure surrounding the apparatus. Typical pressure transducers of the absolute pressure type are available from Sensyn, Inc.

Accordingly, as may now be seen, the CPU 24 is in receipt of all of the information necessary to determine the exact flow of NO containing therapy gas through the fixed restrictor 28 and thus, the flow to the patient 18. The characteristics of the particular fixed restrictor 28, as stated, are available from the manufacturer as a curve or other data that can be inputted to the CPU 24 as a look up table or the like. Since the flow through the fixed restrictor 28 is directly proportional to the absolute pressure of the gas entering the fixed restrictor 28, the CPU 24 also knows the $P_{control}$ from the absolute pressure transducer 30 and thus can readily calculate the flow to the patient 18.

A patient trigger 32 is in communication with the patient 18 by means of a passageway 34 and may include a check valve 36. The patient trigger 32 may be of conventional design and basically detects a negative pressure $P_{trigger}$ from the patient indicating that the patient 18 is initiating inhalation. That patient trigger 32 thus provides a signal to the CPU 24 to alert the CPU 24 that the patient is initiating an inhalation so that the CPU 24 can take the appropriate action to provide a pulse of NO containing therapeutic gas to the patient 18 during that inhalation.

A user input device 38 allows the user to input to the CPU 24 the specific volume of NO containing therapeutic gas that is desired to be delivered to the patient 18 during each inhalation and such device may be a rotary switch or the like. Alternatively, the volume to be delivered may be predetermined by the manufacturer of the delivery system and already established in the system and not be individually selected in the field by a user. Also as a part of the system, there may be an audio alarm 40 and a visual display 42 that may also contain visual alarms as well as display various monitored conditions of the device to the user.

The overall operation of the NO dosing device may now be explained and will refer to the delivery system embodiment where the user makes the desired selection of the volume to be administered to the patient. As noted, upon start-up of the system, the gas cylinder 10 containing the NO therapy gas in a predetermined concentration is opened and the NO containing therapy gas enters the pressure regulator 12 and the conduit 16. Purge valve 22 is opened by a signal from CPU 24 or manually by a prompt displayed on the visual display 42 so that the pressure regulator 12 and the portion of conduit 16 are purged of air.

The user inputs a volume of NO containing therapy gas that is desired to be administered to the patient 18 by means of the user input device 38. As the patient initiates an inhalation, the patient trigger 32 senses the negative pressure and signals the CPU 24 to commence the injection of a dosage of NO containing therapy gas to the patient 18. Initially, the CPU 24 opens the control valve 26 for a predetermined time based upon a calibration curve that is determined at the factory at known ambient pressure and temperature and is incorporated into the device. The ambient pressure is sensed at the location of the use of the NO administration device and a correction made by the CPU 24 to arrive at a period of time that the control valve 26 is opened by the CPU 24 to allow a volume of gas to pass therethrough to the patient 18 and then will move the control valve 26 to its closed position.

The CPU 24 can now calculate the exact volume of gas delivered to the patient 18, using the data that is representative of the characteristics of the fixed restrictor 28 and the input it receives from the absolute pressure transducer 30 of $P_{control}$. With that data and the amount of time that the control valve 26 has been opened, the CPU 24 can readily calculate the exact volume by integrating the flow through fixed restrictor 28 with respect to the time the control valve 26 is in its open position and arrive at the volume of NO containing therapeutic gas administered to the patient 18.

With the calculated volume, the CPU 24 can then compare the volume calculated with the volume that has been inputted by the user as the desired volume for administration to the patient 18. The CPU 24 can thus alter the time the control valve 26 is opened and recalculate until the volume that it calculates is the same as the volume inputted by the user in the user input device 38. At this point, the overall device can administer a user set precise volume of NO containing therapeutic gas at each inhalation triggered by the patient 18.

As further safety features of the NO dosing device, it is possible to detect the failure of the control valve 26 based on data from the $P_{control}$ and the known timing of the control valve sequence. For example, if there is no rise in the value of $P_{control}$ by a known amount, based upon a minimum supply pressure, and the control valve 26 has been given a signal to open by the CPU 24, then the system will recognize a failure to deliver the therapy to the patient 18 and a suitable alarm may be activated at audio alarm 40 and/or by a visual alarm indication on the visual display 42. Conversely, if the $P_{control}$ does not reduce by a known amount, again based upon the minimum supply pressure, and the control valve 26 has been given the signal to close by CPU 24, then the system can detect an cover delivery failure and again an audible or visual alarm activated. Thus one can establish safe limits for delivery of NO and therefore a fault condition can be detected based on the established safe limits.

In a similar manner, the NO dosing device can activate the audio alarm 40 and/or the indicate an alarm condition on the visual display 42 by sensing the volume of gas that passes through the conduit 16, that is, if the signal is provided to close the control valve 26 and the determination of volume of gas passing through the conduit 16 does not cease, it its an indication of a fault and an appropriate response made. In the same manner, the NO dosing device can determine the flow in the conduit 16 to see that the flow ceases or starts based on the triggered position of the control valve 26 to, again, determine a fault condition and provide an alarm to alert the user of that condition.

Figure 2:
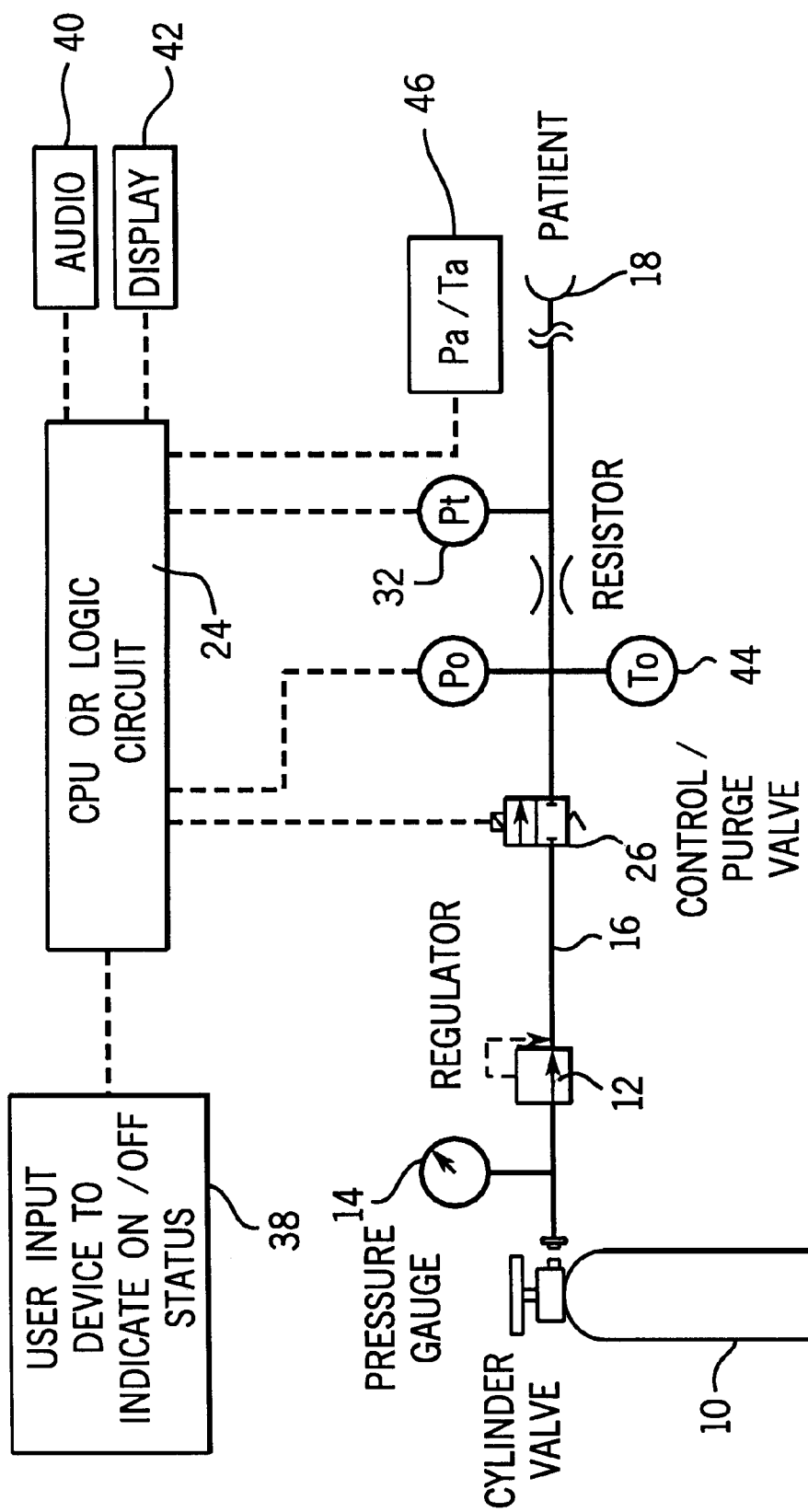
FIG. 2 is a schematic view of an alternate embodiment of a NO delivery system constructed in accordance with the present invention.

Turning now to FIG. 2, there is shown a schematic view of the preferred embodiment of the present invention and where the ambient temperature is taken into account in determining the correct time to open the control valve to obtain a precise dose of therapeutic gas to be administered to the patient. In the FIG. 2 embodiment, many of the components are the same as used with respect to the FIG. 1 embodiment and therefore those components have utilized the same reference numerals. In this embodiment, however, there is the addition of a temperature sensor 44 that senses the temperature $T_0$ of the NO containing therapy gas prior to its passing through the fixed restrictor 28. In addition, an ambient pressure sensor and temperature sensor have been added and those sensors are both depicted by the block 46. The dose can be corrected to a fixed temperature and pressure (and hence be a mass dose) or corrected to the ambient temperature and pressure (and hence be a volumetric dose).

In the operation of the FIG. 2 embodiment, it will be noted that the system takes into account the temperature and pressure of the gas passing through the fixed restrictor 28 as well as the ambient pressure and temperature in order to determine the dosage of NO containing therapy gas to the patient. Again, the gas cylinder 10 is opened and the NO containing therapy gas enters the pressure regulator 12 and the conduit 16. A purge valve is not shown in FIG. 2, however, one obviously can be used in the overall system similar to the FIG. 1 embodiment.

The user inputs the desired volumetric dosage to be delivered to the patient with the user input device 38. The patient trigger 32, again, senses the negative pressure representative of the patient attempting to inhale and patient trigger 32 signals the CPU 24 to commence the introduction of the NO containing therapy gas to the patient 18. Initially, the CPU 24 opens the control valve 26 for a period of time calculated by the CPU 24 based on the dose inputted by the user, Vset. That open time, $T_{INITIAL}$, is based on the curve that was established founded upon the calibration conditions at the factory in initially setting up the system. The system, as manufactured, is calibrated to determine the volumes delivered for the times the control valve 26 is open and is operated at the conditions in the manufacturing facilities during calibration, that is $T_{CAL}$ and $P_{CAL}$ and a set of curves generated for the system.

In use, therefore, as the patient attempts to inhale, the CPU 24 has information from block 46 with respect to the ambient pressure $P_A$ and the ambient temperature $T_A$ and can calculate the $V_{CAL}$ that needs to be provided to the patient for the dose inputted by the user, Vset, based on the actual ambient conditions existing at the patient. Thus, by use of the equation:

$$V_{CAL}=(P_A/P_{CAL})*(T_{CAL}/T_A)*V_{SET}$$

the CPU can determine the $V_{CAL}$ and adjust to the ambient conditions to determine the time that the control valve 26 need be opened to deliver the $V_{SET}$ to the patient at those ambient conditions.

Again the dose actually delivered by the system can be determined as a check against the $V_{SET}$ by the measurements of the temperature and absolute pressure of the gas passing through the fixed restrictor 28, the ambient temperature and pressure, as well as the known pressure flow characteristics of the restrictor or orifice.

Thus, by use of the equation:

$$V_{DEL}=k2\cdot\int\{(P_0/P_A)\cdot T_A/(T_0)^{0.5}\}\cdot dt$$

Where:
$V_{DEL}$=the volume of the pulse where the flow through the orifice was sonic k2=constant for the orifice geometry and gas characteristics $P_0$=orifice gas pressure $T_0$=orifice gas temperature $P_A$=ambient pressure $T_A$=ambient temperature The actual delivered flow can be determined and integrated with the time the control valve is in the open position to derive the $V_{DEL}$ to the patient. The volume delivered can then be compared with the volume established by the user $V_{SET}$ and any error between the values can be used to modify the $T_{INITIAL}$ to become $T_{CONTROL}$ that will correct for any differences.

As a further feature of the present invention, an alarm strategy is used to insure that the delivery device is properly delivering the dose that is desired and inputted by the user. In the implementation of the alarm system, that dose actually delivered by the system, $V_{DEL}$, is compared with the $V_{SET}$ can be used to trigger an alarm if the values are different by a predetermined percentage. That is, if the actual delivered volume is more that a certain percentage, for example, thirty percent (30%), the CPU 24 can recognize that the difference is indicative of a problem in the overall pulse delivery system and trigger the audible alarm 40 and/or provide some visual alarm on the visual display 42.

Numerous further variations and combinations of the features discussed above can be utilized without departing from the spirit of the invention as defined by the claims below. Accordingly, the foregoing description of the preferred embodiment should be taken by way of illustration rather than by way of limitation of the invention as claimed.

We claim:

1. A respiratory therapy apparatus delivering a pulsed dose of nitric oxide gas to a patient, said apparatus having an alarm system and comprising:

conduit means connecting said respiratory therapy apparatus to a source of nitric oxide gas under pressure, means to establish a predetermined desired dose of nitric oxide gas to be delivered along the conduit means to the patient during each inhalation, sensing means for sensing the initiation of an inhalation of the patient, delivery control means coupled to said conduit means and responsive to said sensing means sensing an inhalation of the patient to deliver a pulsed dose of nitric oxide gas along the conduit means to the patient during each inhalation of the patient, a control means for controlling the delivery control means to deliver the dose of nitric oxide gas, a measurement means to detect a fault by measuring the volume of the delivered pulsed dose, comparing the measured volume against the desired volume of the dose, and detecting a fault when the measured volume is greater or less than the desired dose volume be a given amount;

an alarm to alert the user of a fault condition, and means to activate said alarm when said measurement means has detected a fault.

2. A respiratory therapy apparatus as defined in claim 1, wherein said measurement means detects a fault when the measured volume differs from the desired dose volume by at least about 30 percent.

3. A respiratory therapy apparatus as defined in claim 1 wherein said conduit means has an orifice through which said dose is delivered to the patient and wherein said measurement means determines the mass flow of said pulsed dose through said orifice.

4. A respiratory therapy apparatus as defined in claim 3 wherein said respiratory therapy apparatus further includes a sensor for determining ambient temperature and a sensor for determining ambient pressure and said measurement means converts said determined mass flow of said pulsed dose to volumetric flow using said determined ambient temperature and pressure.

5. A respiratory therapy apparatus as defined in claim 1 wherein said apparatus further includes a sensor for determining ambient temperature and a sensor for determining ambient pressure and said measurement means corrects said control means in accordance with said ambient temperature and said ambient pressure determinations.

6. A respiratory therapy apparatus delivering a dose of nitric oxide gas to a patient, said apparatus having an alarm system and comprising:

a conduit adapted to be connected to a source of nitric oxide gas under pressure and to a patient, said conduit including a valve controlling the flow of the nitric oxide gas from the source to the patient, control means to open and close said valve at timed intervals by sending a signal to open said valve and a signal to close said valve to deliver accurate doses of the nitric oxide gas along the conduit to the patient, a sensor adapted to detect a condition of the dose of nitric oxide gas in said conduit, an alarm activatable to alert the user of a fault condition, and means to activate said alarm when a signal has been sent by said control means to close said valve and said sensor does not detect a corresponding change in the detected condition of the dose in said conduit indicative of the valve being moved to its closed position.

7. A respiratory therapy apparatus as defined in claim 6 wherein said sensor is a pressure sensor.

8. A respiratory therapy apparatus as defined in claim 6 wherein said sensor is a flow sensor.

9. A respiratory therapy apparatus delivering a dose of nitric oxide gas to a patient, said apparatus having an alarm system and comprising:

a conduit adapted to be connected to a source of nitric oxide gas under pressure and to a patient, said conduit including a valve controlling the flow of the nitric oxide gas from the source to the patient, control means to open and close said valve at timed intervals by sending a signal to open said valve and a signal to close said valve to deliver accurate doses of the nitric oxide gas along the conduit to the patient, a sensor adapted to detect a physical condition in said conduit, an alarm activatable to alert the user of a fault condition, and means to activate said alarm when a signal has been sent by said control means to open said valve and said sensor does not detect a corresponding change in a physical condition in said conduit indicative of the valve being moved to its open position.

10. A respiratory therapy apparatus as defined in claim 9 wherein said sensor is a pressure sensor.

11. A respiratory therapy apparatus as defined in claim 9 wherein said sensor is a flow sensor.

* * * * *